(12) United States Patent
Shoemaker et al.

(10) Patent No.: US 8,689,649 B2
(45) Date of Patent: Apr. 8, 2014

(54) METHODS AND SYSTEMS TO PREVENT PUNCH LOSS DURING AUTOMATED SAMPLE PROCESSING

(75) Inventors: Philip Alexander Shoemaker, Scotia, NY (US); Weston Blaine Griffin, Niskayuna, NY (US); Erin Jean Finehout, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 544 days.

(21) Appl. No.: 12/630,899

(22) Filed: Dec. 4, 2009

(65) Prior Publication Data
US 2011/0132111 A1 Jun. 9, 2011

(51) Int. Cl.
*G01N 1/08* (2006.01)
(52) U.S. Cl.
USPC ............................................. 73/864.41
(58) Field of Classification Search
USPC ............................................. 73/864.41
See application file for complete search history.

(56) References Cited

U.S. PATENT DOCUMENTS

| | | | |
|---|---|---|---|
| 4,341,735 A * | 7/1982 | Seifried | 422/66 |
| 5,460,057 A | 10/1995 | Ostrup | |
| 5,638,170 A | 6/1997 | Trinka et al. | |
| 5,641,682 A | 6/1997 | Pagels et al. | |
| 5,789,251 A | 8/1998 | Astle | |
| 6,372,504 B1 | 4/2002 | Tervamaki et al. | |
| 2002/0052696 A1* | 5/2002 | Gallagher et al. | 702/30 |
| 2004/0014228 A1* | 1/2004 | Brignac et al. | 436/43 |
| 2006/0188404 A1 | 8/2006 | Gjerde | |

FOREIGN PATENT DOCUMENTS

| | | |
|---|---|---|
| WO | 2004041435 A2 | 5/2004 |
| WO | 2006056658 A1 | 6/2006 |
| WO | 2010009173 A1 | 1/2010 |

OTHER PUBLICATIONS

GB1020371.9 GB Search Report, Mar. 15, 2011.

* cited by examiner

*Primary Examiner* — Hezron E Williams
*Assistant Examiner* — Paul West
(74) *Attorney, Agent, or Firm* — Jenifer Haeckl

(57) ABSTRACT

Automated methods and systems for punching out pieces of a porous substrate for biological samples comprising: loading the porous substrate onto a support comprising a die and an opening; moving a receptacle support in at least a z-direction to position a receptacle relative to the support so that an opening in the receptacle is aligned and substantially flush with the opening in the support; actuating a punching head so that the punching head passes through the die, thereby punching a piece out of the porous substrate; and actuating an ejector pin to eject the punched piece from the porous substrate support and into the receptacle aligned with the opening in the support.

28 Claims, 5 Drawing Sheets

METHODS AND SYSTEMS TO PREVENT PUNCH LOSS DURING AUTOMATED SAMPLE PROCESSING

BACKGROUND

The invention relates generally to methods and systems to prevent punch loss during automated sample processing.

Porous substrates, such as cellulose matrices (e.g. 31 ETF, FTA and FTA elute cards available from Whatman) are often used to store biological samples, such as blood. A new application area for these cards is in the pharmaceutical industry, which is using them to store dried blood samples from pharmacokinetic and toxicokinetic studies. When it is time to analyze the amount of drug or drug metabolite in the dried blood spot, the current methods require the user to cut the sample out of the card, usually a 1-6 mm diameter circle, place the cut disc in a vial or well with extraction fluid, and then shake/vortex for a set period of time. The extraction fluid is then removed and analyzed using a method such as LC-MS.

The pharmaceutical industry is expecting to process a large number of samples per day and is therefore looking for ways to automate the process. The current workflow of disc cutting and extraction, poses several problems when facing the challenge of automation. The primary problems arise from the cutting step. The small cut discs are highly prone to the effects of static electricity or even a light breeze. There are numerous reports of cut discs being lost during the cutting step or during transport of the cut discs. Currently, sample discs are lost due to factors such as static electricity and air movement. For example, static charges may build up in the plastic multiwall plates or tubes, causing the discs to sticks to the plates or tubes walls. The discs sometimes stick to the punching device or, later in the process, the discs sometimes stick to the liquid handling probes, which, when the probes are withdrawn from the well, the discs are inadvertently removed from the well.

The current instruments on the market focus on reducing sample disc loss by reducing the amount of air movement in the system (enclosed system) and adding anti-static devices (such as humidifiers).

Automated punching systems typically use a plate handling system (or tube strip handling system) that positions the plates/tubes below a stationary puncher so that each sample disc drops into a different well/tube. However, these plate-handling systems only move in two directions (forwards and sideways). This type of system leaves a gap between the bottom of the punching device and the top of the 96-well plate. The gap is necessary is such systems because the top of the plate would otherwise rub against the bottom of the punching device as it moves laterally from well to well.

Attempts have been made to use a modified plate cover to keep a punch inside a well, for example, by having small teeth on the cover of each well. However, this modification does not allow for liquids to subsequently be added to the wells with ease. Such modifications also do not allow the punch to be removed from, or otherwise moved within the well, once inserted into the well, which is important for some extraction methods. Other types of plate covers, for use on 96-well plates, are modified to prevent liquid from escaping from the well. These covers are thin films with slits cut into them to prevent evaporation and to allow small slow-moving probes, such as pipette tips or liquid handling probes, to enter the well. However, these thin films are quite stiff and intended to fully reseal as the pipettes are withdrawn from the wells. Such covers do not allow the punch to be inserted or otherwise moved within the receptacle without causing the punches to catch or otherwise stick onto top side of the covers or the ejector, and would necessarily require pipettes to add or remove any liquids from the wells in order to breach the sealed slits.

BRIEF DESCRIPTION

The automated methods and systems of the invention generally relate to preventing the loss of sample discs by ensuring that the sample discs go into the well in the first place and that, even if static or air movement is present, the punch stays in the well.

An embodiment of an automated system of the invention, for punching out pieces of a porous substrate for biological samples, comprises: a puncher; an ejector pin having a cross-sectional dimension; a porous substrate support with an opening larger the cross-sectional dimension of the punching head; one or more sample piece receptacles; and a handling subsystem that moves in x, y, and z directions and aligns an opening in one or more of the receptacles substantially flush with the opening in the support. The sample piece receptacles may be seated on the handling subsystem and move with the handling subsystem in the x, y and z directions. The substrate support may be in a fixed relationship with the handling subsystem and move in the x, y and z directions with the handling subsystem.

The puncher may comprise a punching head and the porous substrate support may comprise a die corresponding to the punching head. In at least one embodiment, the puncher has an inner cannular bore through which the ejector pin moves.

The punching die may have a cross-sectional dimension that is larger than the cross-sectional dimension of the ejector pin, wherein the ejector pin, when in an extended position, has a distally located end sized to pass through the opening in the porous substrate support and into the opening of one of the receptacles when aligned with the opening in the support.

The receptacles may comprise a well on a multi-well plate and the multi-well plate may be seated on the handling subsystem. The multi-well plate comprises a plurality of well such as, but not limited to, ninety-six (96) wells. The receptacles may also comprise one or more vials seated on the handling subsystem.

The sample receptacles may also comprise a plurality of cover flaps that comprise a thin film material having a low modulus and inherently high flexibility. The cover flaps may curve inward and form a low resistance opening in the cover. The thin film material may have a thickness that is about equal to or less than 100 um thick and may comprise, but are not limited to, one or more of polyester, polypropylene, and polyester/polypropylene laminates. For example, in one embodiment, the thin film material has a thickness of about equal to or less than 65 um.

An example of the automated method for punching out pieces of a porous substrate for biological samples comprises: loading the porous substrate onto a support comprising a die and an opening; moving a receptacle support in at least a z-direction to position a receptacle relative to the support so that an opening in the receptacle is aligned and substantially flush with the opening in the support; actuating a punching head so that the punching head passes through the die, thereby punching a piece out of the porous substrate; actuating an ejector pin to eject the punched piece from the porous substrate support and into the receptacle aligned with the opening in the support; and repeating at least steps b through d, as needed. Ejecting the punched piece may comprise extending at least a distally located end of the ejector pin through the opening in the porous substrate support and into the opening of one of the receptacles when aligned and flush with the opening in the support. The punched piece may comprise a portion of the biological sample. The receptacles may be seated on the handling subsystem and move with the handling subsystem in the x, y and z directions. The substrate support may be in a fixed relationship with the handling subsystem and move in the x, y and z directions with the handling subsystem.

The receptacles may comprise wells on a multi-well plate that is seated on the handling subsystem that moves in x, y and z directions. The receptacles may also comprise one or more vials seated, for example, on the handling subsystem.

The sample receptacles used in the method may also comprise a plurality of cover flaps that comprise a thin film material having a low modulus and inherently high flexibility and may curve inward to form a low resistance opening in the cover. The thin film material may have a thickness that is about equal to or less than 100 um thick and may comprise, but are not limited to, one or more of polyester, polypropylene, and polyester/polypropylene. For example, in one embodiment, the thin film material has a thickness of about equal to or less than 65 um.

DRAWINGS

These and other features, aspects, and advantages of the present invention will become better understood when the following detailed description is read with reference to the accompanying drawings in which like characters represent like parts throughout the drawings, wherein:

FIGS. 3A-3C are cross-sectional drawings of the embodiment of the system shown in FIG. 1 or FIG. 2 in progressive stages of use.

DETAILED DESCRIPTION

The methods and systems of the invention generally prevent sample loss when processing samples, such as dried blood spots, by preventing the loss of the small discs that have been cut from the initial sample matrix. These methods and systems can be incorporated into other systems designed to automate the cutting of discs from dried samples on carrier substrates such as cellulose matrices or polymer membranes.

For example, during the preparation of some samples, such as dried blood spots on cellulose cards, a small punch (1-6 mm in diameter) is cut out and placed into a wellplate or tube for subsequent processing. One or more of the embodiments of the methods and systems use a z-axis movement to place the receiving tube or well plate directly under, and in contact with, the punching apparatus. The methods and systems may also use a modified well plate cover and methods of punching and ejecting that are compatible with such modified well plate covers, to further prevent the punches from leaving the well once they have been placed there A non-limiting embodiment of a system, which is generally shown and referred to in FIG. 1 as system 10, comprises a top puncher 12, an ejector pin assembly 14, a well plate or tube strip 16, and a plate/tube handling subsystem 18 that moves in x, y, and z directions. The well plate may comprise a plurality of wells such as, but not limited to, the ninety-six (96) wells shown is well plate 16. The receptacles may also comprise one or more vials seated on the handling subsystem.

Figure 1:
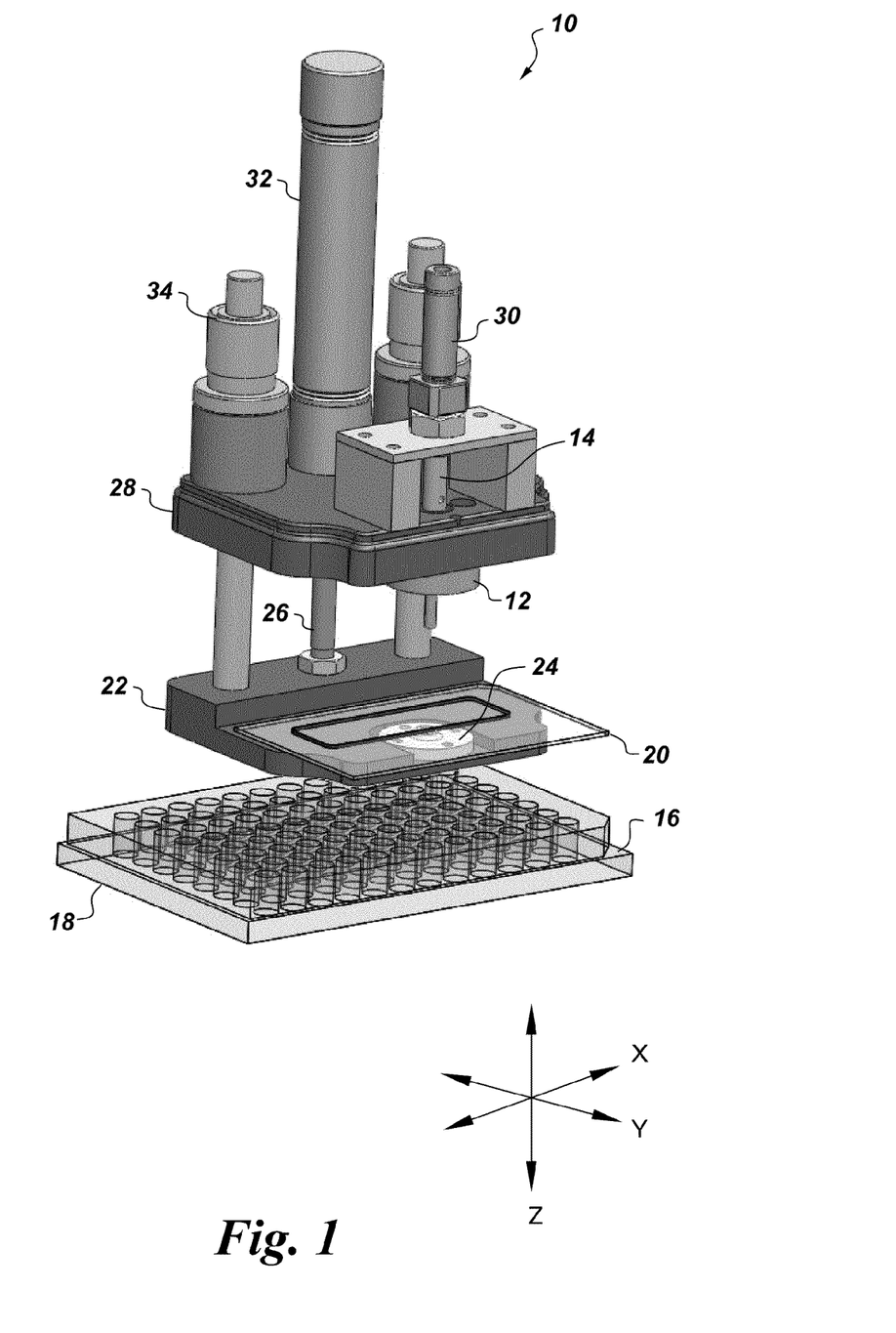
FIG. 1 is a perspective drawing of an embodiment of a system of the invention to prevent punch loss.

System 10 also comprises a die set bottom 22 that supports the porous substrate 20 (e.g. FTA card) and bottom punch die 24. Die set top 28 supports ejector pin assembly 14 that is driven by an ejector pin pneumatic cylinder 30. The main piston rod 26 is driven by the main pneumatic cylinder, and extends and retracts during the punching operation. In this embodiment the sample piece receptacles are the wells in the well plate and are seated on the handling subsystem 18 and move with the handling subsystem in the x, y and z directions. By moving in the z direction, in addition to the x and y directions, the handling subsystems allows the opening in each receptacle to line up, and be placed substantially flush, with the opening in die set bottom, which likewise corresponds with the ejector pin, the top punch tool and the bottom punch die. This alignment allows a punch, or piece of the porous substrate, to fall and/or be further ejected directly into a given receptacle or well after it is cut out of the porous substrate, without the risk of the punch from inadvertently falling into an adjacent well.

Figure 3A:
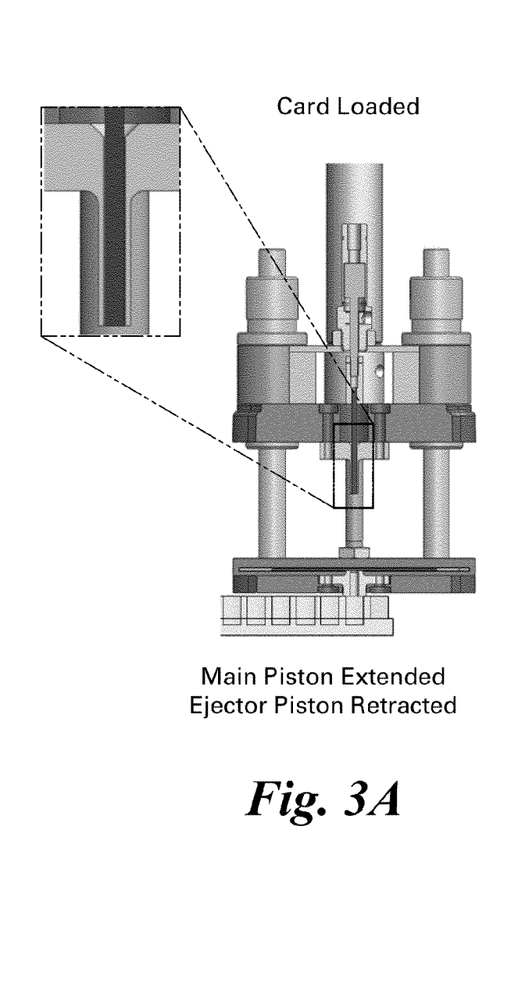
FIG. 3A shows the system after a porous substrate is loaded into the device.

The puncher may comprise a punching head, such as top punch tool 12, and the porous substrate support, such as die set bottom 22, may comprise a die (e.g. bottom punch 24) which corresponds to the punching head. In this embodiment, the puncher has an inner cannular bore through which the ejector pin moves relative to the puncher as shown in FIG. 3A. The punching die has a cross-sectional dimension that corresponds to the cross-sectional dimension of the punching head, wherein the ejector pin, when in an extended position, has an end that is distally located from the top punch tool assembly, and is sized to pass through the cannular bore of the top punch tool and thereby the opening in the porous substrate support and into the opening of one of the receptacles when aligned with the opening in the support.

Figure 2:
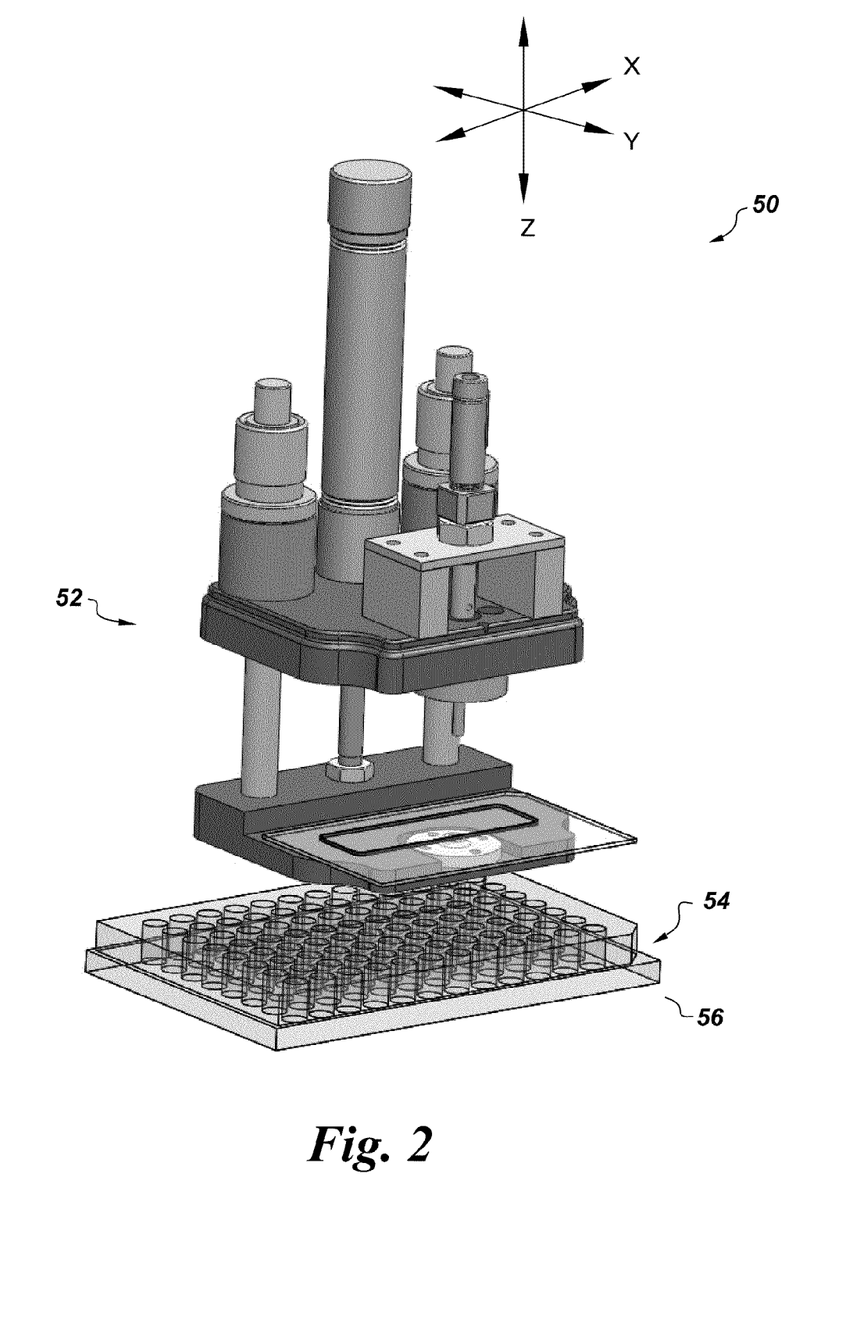
FIG. 2 is a perspective drawing of another embodiment of the system of the invention to prevent punch loss.

Another embodiment of the system is generally shown and referred to in FIG. 2 as system 50. In system 50, the substrate support, together with the punching and ejector mechanism, comprise and are in a fixed relationship with the handling subsystem 52 and, as such, move in the x, y and z directions with the handling subsystem. By moving in the z direction, in addition to the x and y directions, this embodiment of the handling subsystem moves the die set bottom, together with ejector pin, the top punch tool and the bottom punch die, so that the corresponding openings align with the opening in a given receptacle into which a punched piece of the porous substrate is to fall. Similarly, this alignment allows a punch, or piece of the porous substrate, to fall and/or be further ejected directly into a given receptacle or well after it is cut out of the porous substrate, without the risk of the punch from inadvertently falling into an adjacent well.

Figure 3B:
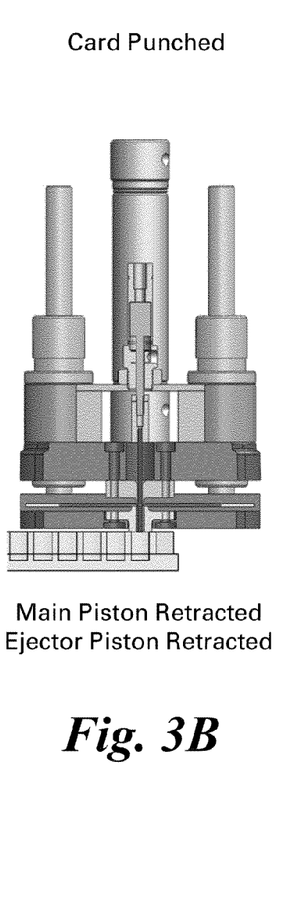
FIG. 3B show the porous substrate being punched.
Figure 3C:
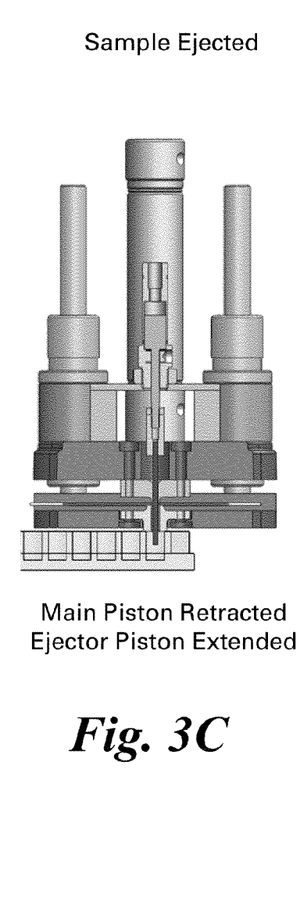
FIG. 3C shows the punched disc being ejected into a receptacle.

FIGS. 3A through 3C show the embodiment of the system shown in FIG. 1 or 2 in progressive stages of use. FIG. 3A shows the system after a porous substrate is loaded into the device. The main piston is extended and the ejector piston is retracted. FIG. 3B show the porous substrate being punched. The main piston is retracted and the ejector piston is retracted.

FIG. 3C shows the punched disc being ejected into a receptacle. The main piston is retracted and the ejector piston is extended pushes the punched piece into and through the opening in the receptacle that is aligned with the opening in the porous substrate support.

Figure 4A:
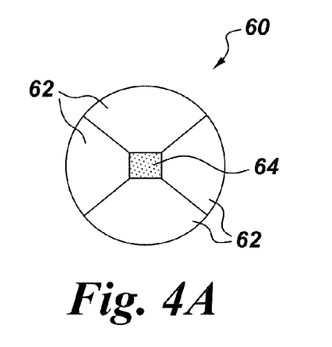
FIG. 4A is a top view of an example of the cover flaps of the receptacle.
Figure 4B:
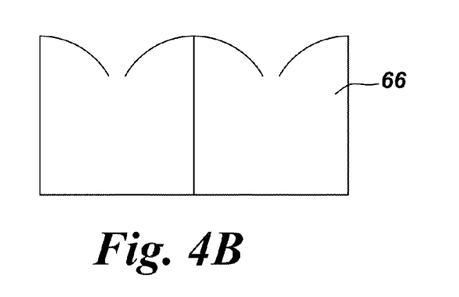
FIG. 4B is a cross-sectional view of two receptacles showing the cover flaps of FIG. 4A as they curve inward towards the bottom of the receptacles.

As shown in FIGS. 4A and 4B, the sample receptacles may also have a cover 60 that comprises a plurality of cover flaps comprising a thin film material having a low modulus and inherently high flexibility and low resistance. Such characteristics may, depending on their extent, result in cover flaps such as flaps 62 shown in FIGS. 4A and 4B, that curve inward towards the bottom or inside of the receptacles. FIG. 4A is a top view of the cover flaps that, because of their low modulus and/or thickness, depending on the material and thickness of the material used, droop naturally inward towards the bottom of each receptacle 66, forming a small opening 64 in the cover through which a punched piece can fall or otherwise be pushed by the ejector pin into the receptacle. The thin film material may have a thickness that is about equal to or less than 100 um thick and may comprise, but are not limited to, one or more of polyester, polypropylene, and polyester/polypropylene laminates. For example, in one embodiment, the thin film material has a thickness of about equal to or less than 65 um. The thickness of the material will depend on the type of material used. The higher the modulus of the material, the thinner the thickness of the material will be to achieve a cover flap that provides low resistance to the punch piece dropping into the receptacle and/or the ejector pin.

If the low modulus and flexibility are low enough, in a given embodiment, such as the embodiment shown in FIGS. 4A and 4B, to cause the flaps to curve inward, such flaps will not only allow a punch piece to fall easily through the opening formed by the inwardly curving flaps, into the receptacle aligned with the opening in the porous substrate support, but also creates inwardly directed edges that prevent the punched piece for inadvertently escaping from the receptacle, once the piece falls or is pushed by the ejector pin into the receptacle. The opening formed by the inwardly curving cover flaps may correspond in size to the size of the distal end of the ejector pin and/or the punch piece. The term correspond does not necessarily mean equal in size, it means that the sizes should correspond so that the sizes of various components are optimal for inserting the punch piece into the receptacle and yet retain the punch piece in the receptacle once is it inserted.

Figure 5A:
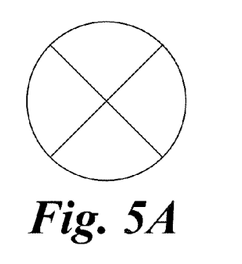
FIGS. 5A and 5B are top views of two non-limiting examples of cutting patterns for the receptacle covers.
Figure 5B:
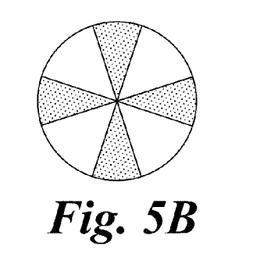

In addition to the type and thickness of the thin film material, the size of the opening created by the inwardly curving cover flaps may be varied, for example, by the slit or cut configuration of the flaps. FIGS. 5A and 5B show two non-limiting examples of slit configurations for the cover flaps. These configurations shown as if the cover flaps are sitting on a flat surface, before they are allowed to droop or otherwise curve inward towards the bottom of a receptacle.

Figure 6:
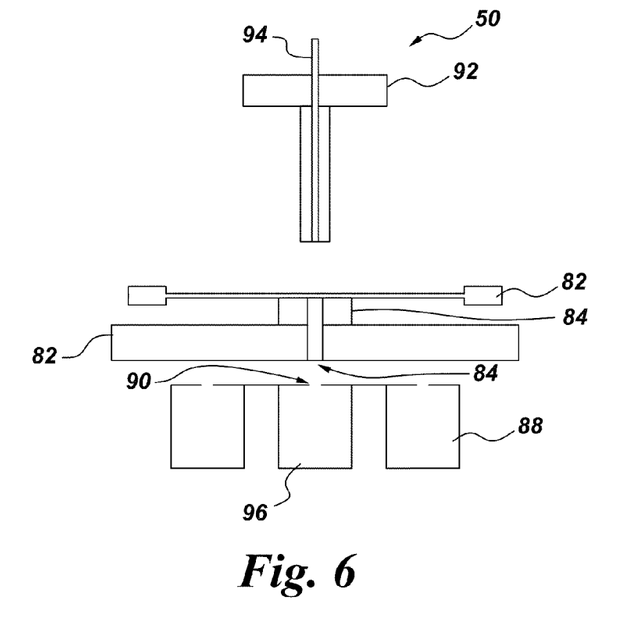
FIG. 6 is a schematic cross-sectional view of an embodiment of the system of the invention.
Figure 7A:
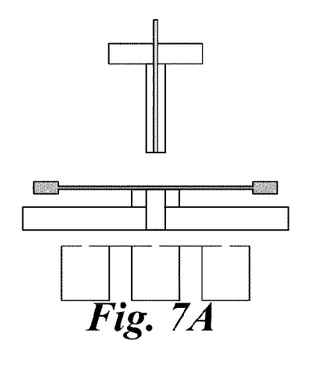
FIGS. 7A-7F are schematic cross-sectional views showing the embodiment of the system of FIG. 6 is progressive stages of action.
Figure 7B:
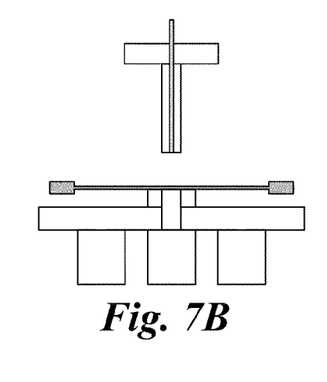
Figure 7C:
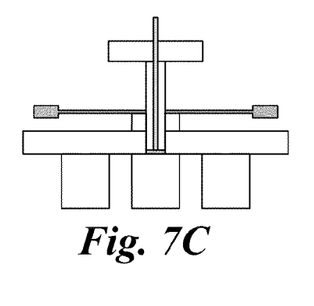
Figure 7D:
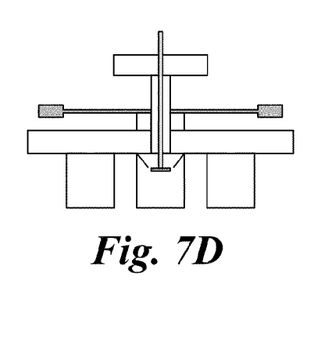
Figure 7E:
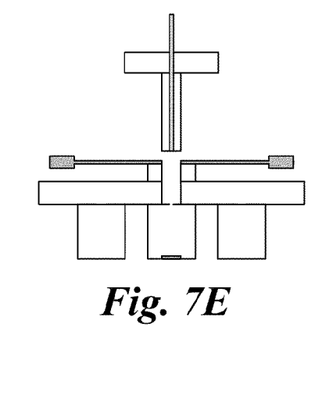
Figure 7F:
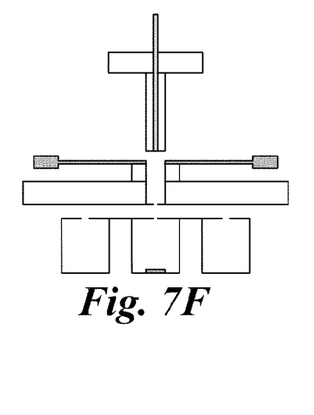

An example of the automated method for punching out pieces of a porous substrate for biological samples is illustrated, for example, in FIGS. 7A through 7F and uses an embodiment of the system generally shown and referred to in FIG. 6 as system 80 comprises: loading the porous substrate 82 (e.g. FTA card) onto a support 82 (e.g. die plate) comprising a die 84 and an opening 86 (FIG. 7A); moving a receptacle support 88 in at least a z-direction to position a receptacle (e.g. a well in a well plate) relative to the support 82 so that an opening 90 in the receptacle is aligned and substantially flush with the opening in the support (FIG. 7B); actuating a punching head 92 so that the punching head passes through the die 82, thereby punching a piece out of the porous substrate (FIG. 7C); actuating an ejector pin 94 to eject the punched piece from the porous substrate support and into the receptacle 96 aligned with the opening in the support (7D); and repeating at least steps b through d, as needed, retracting the puncher and ejector pin after each punch (FIG. 7E). Ejecting the punched piece may comprise at least a distally located end of the ejector pin through the opening in the porous substrate support and into the opening of one of the receptacles when aligned and flush with the opening in the support (FIG. 7D). The punched piece may comprise a portion of the biological sample. The receptacles may be seated on the handling subsystem and move with the handling subsystem in the x, y and z directions. The substrate support may alternatively, or in addition, be in a fixed relationship with the handling subsystem and move in the x, y and z directions with the handling subsystem.

Similarly, the receptacles may comprise wells on a multi-well plate that is seated on the handling subsystem that moves in x, y and z directions. The receptacles may also comprise one or more vials seated, for example, on the handling subsystem.

Similarly, sample receptacles used in the methods may also have a cover that comprises a plurality of cover flaps having a low resistance so that the punched piece can fall or otherwise be pushed by the ejector pin into the receptacle.

The puncher cuts out defined area of substrate containing dried sample. The puncher used in the methods and systems may be a tool and die style puncher, circular blade, laser cutter, or other suitable cutting device. Generally, the ejector pin helps to ensure the cut disc enters the receiving well/tube. If the cut disc has not already entered the well/tube, the ejector pin pushes the cut disc from its post-cutting position into the well/tube.

As one example of an application in which the methods and systems may be used, a tool and die style puncher cuts out a disc from dried blood spots on cellulose cards typically used in forensic tests. Prior to cutting, a well plate is moved up against the die of the puncher so that the rim of the well touches the die. The handling subsystem moves the multi-well plate along multiple axes (e.g. x, y, and z). The x and y axis of motion allow each well/tube to be aligned with the centerline axis of the puncher. The z-axis of motion allows the plate/tubes to be pushed up until touching the bottom of the punching platform. After the disc is cut, it is confined to an area directly above the well and in the well. This ensures that during the cutting step, the cut disc does not fall into the wrong well. A 1.75 mm diameter ejector pin is used in this example, to push the cut discs that may still reside in the opening of the support or on the cover of the receptacle, because it did not naturally fall into the well for any number of reasons, in the receptacle.

In one embodiment of the system and method, the opening in the receptacle cover is deformed when the punch or pin is pressed through/against it to allow entrance. The pin pushes the cut disc past the opening and any deformed edges of the cover. The pin has a smaller diameter than the cut disc and thus, in the deformed state the cover is still touching the punch/pin and therefore will "scrape off" any cut discs that are sticking to the pin, as the pin is retracted. After the punch/pin are removed, the seal returns to it's initial configuration. The cut disc, by itself, will not apply enough force to the opening to force it to deform. Therefore the cut disc cannot leave the well due to effects such as static, air movement, momentum, or vibration.

The cover or cover flaps may be applied to the receptacles or well plates by various means. For example, the cover may be fixed to the receptacles or well plate using a heat seal. Other examples include, but are not limited to, a pre-cut capmat or a patterned adhesive seal (e.g. where there is no adhesive above the wells). The receptacle covers and cover flaps are also compatible with any downstream liquid handling steps. The opening will deform for standard liquid handling probes or pipette tips. The coverings may also be used on tubes or tube strips.

A variety of openings and the size and shape of the punched pieces are compatible with the methods and systems, and will depend on a given application or use.

The methods and systems of the invention may be used in conjunction (e.g. in-line) with analytical systems that analyze the samples and materials extracted from the samples on the porous substrates for many different purposes such as, but not limited to, immunoassays (e.g. to identify the presence or absence of a component), liquid chromatography with UV detection (e.g. to characterize and quantify components), liquid chromatography with mass spectrometry (e.g. to identify and/or quantify components), and polymerase chain reaction (PCR) for DNA analysis. The methods and systems may be adapted for high-throughput applications.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An automated system for punching out pieces of a porous substrate for biological samples comprising,
   a puncher;
   an ejector pin having a cross-sectional dimension, a length and a distal end;
   a porous substrate support with an opening larger the cross-sectional dimension of the ejector pin;
   a plurality of sample piece receptacles, each of which has an opening; and
   an automated handling subsystem that moves in x, y, and z directions and aligns an opening in one or more of the receptacles substantially flush with the opening in the support, wherein the sample piece receptacles are positioned below the porous substrate support whereby the ejector pin, the opening in the porous substrate support and the sample piece receptacles are all vertically aligned with each other in the z direction;
   wherein the length of ejector pin is configured, together with the opening of sample piece receptacle, so that the distal end of the ejector pin, when in an actuated position, extends into the opening of the receptacle; and wherein one or more of the sample piece receptacles are seated on the handling subsystem and move in the x, y and z directions with the handling subsystem; and wherein the substrate support is in a fixed relationship with the handling subsystem and moves in the x, y and z directions with the handling subsystem.

2. The system of claim 1, wherein the puncher has an inner cannular bore through which the ejector pin moves.

3. The system of claim 1, wherein the puncher comprises a punching head and the porous substrate support comprises a die corresponding to the punching head.

4. The system of claim 3, wherein the punching die has a cross-sectional dimension that corresponds to the cross-sectional dimension of the punching head.

5. The system of claim 1, wherein one or more of the receptacles comprises a well on a multi-well plate.

6. The system of claim 5, wherein the multi-well plate is seated on the handling subsystem.

7. The system of claim 5, wherein the multi-well plate comprises at least ninety-six (96) wells.

8. The system of claim 1, wherein one or more of the receptacles comprises a vial.

9. The system of claim 8, wherein the vial is seated on the handling subsystem.

10. The system of claim 1, wherein the sample receptacles comprise a plurality of cover flaps that comprise a thin film material having a low modulus and inherently high flexibility.

11. The system of claim 10, wherein the cover flaps curve inward and form a low resistance opening in the cover.

12. The system of claim 11, wherein the thin film material has a thickness that is about equal to or less than 100 um thick and comprises one or more of polyester, polypropylene, and polyester/polypropylene.

13. The system of claim 12, wherein the thin film material has a thickness of about equal to or less than 65 um.

14. An automated method for punching out pieces of a porous substrate for biological samples comprising,
   a. loading the porous substrate onto a support comprising a die and an opening;
   b. moving a receptacle support, comprising a plurality of receptacles, configured to move in an x, y and z direction, in at least a z-direction to position one of the receptacles, each of which is configured to receive only one piece of substrate, relative to the support so that an opening in the receptacle is aligned and substantially flush with the opening in the support;
   c. actuating a punching head so that the punching head passes through the die, thereby punching a piece out of the porous substrate;
   d. actuating an ejector pin, having a distal end, to eject the punched piece directly from the die and into the receptacle aligned with the opening in the support whereby the distal end of the ejector pin extends past the opening to deposit the punched piece into an interior of the receptacle; and
   e. automatically repeating at least steps b through d, as needed.

15. The automated method of claim 14, wherein the punched piece comprises a portion of the biological sample.

16. The method of claim 15, wherein one or more of the receptacles comprises a well on a multi-well plate.

17. The method of claim 16, wherein the multi-well plate is seated on a handling subsystem that moves in x, y and z directions.

18. The method of claim 16, wherein the multi-well plate comprises at least ninety-six (96) wells.

19. The method of claim 14, wherein one or more of the receptacles are seated on a handling subsystem and move in the x, y and z directions with the handling subsystem.

20. The method of claim 14, wherein the substrate support is in a fixed relationship with the handling subsystem and moves in the x, y and z directions with the handling subsystem.

21. The method of claim 14, wherein the punching head has an inner, cannular bore through which the ejector pin moves.

22. The method of claim 14, wherein the die has a cross-sectional dimension that corresponds to a cross-sectional dimension of the punching head.

23. The method of claim 14, wherein one or more of the receptacles comprises a vial.

24. The method of claim 23, wherein the vial is seated on a handling subsystem that moves in x, y and z directions.

25. The method of claim 14, wherein the sample receptacles comprise a plurality of cover flaps that comprise a thin film material having a low modulus and inherently high flexibility.

26. The method of claim 25, wherein the cover flaps curve inward and form a low resistance opening in the cover.

27. The method of claim 26, wherein the thin film material has a thickness that is about equal to or less than 100 um thick and comprises one or more of polyester, polypropylene, and polyester/polypropylene.

28. The method of claim 27, wherein the thin film material has a thickness of about equal to or less than 65 um.

* * * * *